(12) United States Patent
Van Duren

(10) Patent No.: US 7,520,889 B2
(45) Date of Patent: Apr. 21, 2009

(54) THERMAL BLANKET FOR WARMING THE LIMBS

(75) Inventor: Albert P. Van Duren, Chaska, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 572 days.

(21) Appl. No.: 11/057,397

(22) Filed: Feb. 11, 2005

(65) Prior Publication Data

US 2006/0184216 A1    Aug. 17, 2006

(51) Int. Cl.
*A61F 7/00* (2006.01)
(52) U.S. Cl. .................. 607/104; 607/107; 607/108
(58) Field of Classification Search .............. 607/96, 607/107–108
See application file for complete search history.

(56) References Cited

U.S. PATENT DOCUMENTS

| | | | | |
|---|---|---|---|---|
| 2,573,414 A | 10/1951 | Dunn | .................. | 128/144 |
| 2,826,758 A | 3/1958 | Kahn | .................. | 2/81 |
| 3,468,299 A | 9/1969 | D'Amato | .................. | 126/204 |
| 3,610,323 A | 10/1971 | Troyer | .................. | 165/46 |
| 3,855,635 A | 12/1974 | Ramirez | .................. | 2/114 |
| 3,911,499 A | 10/1975 | Benevento et al. | .................. | 2/114 |
| 3,950,789 A | 4/1976 | Konz et al. | .................. | 2/93 |
| 4,055,173 A | 10/1977 | Knab | .................. | 128/139 |
| 4,146,933 A | 4/1979 | Jenkins et al. | .................. | 2/2 |
| 4,369,528 A | 1/1983 | Vest et al. | .................. | 2/69 |
| 4,494,248 A | 1/1985 | Holder | .................. | 2/69 |
| 4,524,463 A | 6/1985 | Ogden | .................. | 2/105 |
| 4,558,468 A | 12/1985 | Landry et al. | .................. | 2/51 |
| 4,578,825 A | 4/1986 | Vote | .................. | 2/114 |
| 4,587,671 A | 5/1986 | Rodriguez et al. | .................. | 2/69 |
| 4,651,727 A | 3/1987 | Howorth | .................. | 128/201.23 |
| 4,653,120 A | 3/1987 | Leaf | .................. | 2/114 |
| 4,696,066 A | 9/1987 | Ball et al. | .................. | 2/272 |
| 4,787,101 A | 11/1988 | Feinberg | .................. | 2/105 |
| 4,914,752 A | 4/1990 | Hinson et al. | .................. | 2/2 |
| 4,964,282 A | 10/1990 | Wagner | .................. | 62/259.3 |
| 5,062,424 A | 11/1991 | Hooker | .................. | 128/379 |
| 5,255,390 A | 10/1993 | Gross et al. | .................. | 2/2 |
| 5,304,213 A | 4/1994 | Berke et al. | .................. | 607/107 |

(Continued)

FOREIGN PATENT DOCUMENTS

GB        475811        11/1937

(Continued)

OTHER PUBLICATIONS

Written Opinion of the International Search Authority (EPO) in PCT/US2006/041028, mailed Feb. 20, 2007.

(Continued)

*Primary Examiner*—Roy D Gibson
(74) *Attorney, Agent, or Firm*—INCAPLAW; Terrance A Meador

(57) ABSTRACT

A thermal blanket for warming the limbs includes a surface, an inactive region of the surface adapted to lie against the thoracic and/or abdominal area of a person extending at least from the thighs to the abdomen of the person, active regions of the surface adapted to circulate pressurized air to limbs of the person, and an inflatable pneumatic structure adapted to distribute pressurized air to the active regions. When warmed, pressurized air is introduced into the pneumatic structure, prewarming and/or comfort warming is provided.

20 Claims, 2 Drawing Sheets

U.S. PATENT DOCUMENTS

| | | | | |
|---|---|---|---|---|
| 5,360,439 | A | 11/1994 | Dickerhoff et al. | 607/107 |
| 5,367,710 | A | 11/1994 | Karmin | 2/114 |
| 5,411,541 | A | 5/1995 | Bell et al. | 607/104 |
| 5,443,488 | A | 8/1995 | Namenye et al. | 607/107 |
| 5,572,742 | A | 11/1996 | McFadden | 2/114 |
| 5,575,006 | A | 11/1996 | Wolfe | 2/114 |
| 5,611,087 | A | 3/1997 | Adkins | 2/114 |
| 5,620,482 | A | 4/1997 | Augustine et al. | 607/107 |
| 5,697,963 | A | 12/1997 | Augustine | 607/108 |
| 5,785,716 | A | 7/1998 | Bayron et al. | 607/108 |
| 5,891,187 | A | 4/1999 | Winthrop et al. | 607/96 |
| 5,970,519 | A | 10/1999 | Weber | 2/81 |
| 5,974,605 | A | 11/1999 | Dickerhoff et al. | 5/421 |
| 6,049,907 | A | 4/2000 | Palomo | 2/51 |
| 6,154,883 | A | 12/2000 | Spann et al. | 2/69 |
| 6,176,870 | B1 * | 1/2001 | Augustine | 607/107 |
| 6,216,270 | B1 | 4/2001 | Moquin et al. | 2/69 |
| 6,235,659 | B1 | 5/2001 | McAmish et al. | 442/79 |
| 6,378,136 | B2 | 4/2002 | Matsushita | 2/114 |
| 6,484,321 | B1 | 11/2002 | Shamam | 2/114 |
| 6,511,501 | B1 | 1/2003 | Augustine et al. | 607/96 |
| 6,524,332 | B1 | 2/2003 | Augustine et al. | 607/107 |
| 6,551,347 | B1 | 4/2003 | Elkins | 607/104 |
| 6,571,574 | B1 | 6/2003 | Blackstone | 62/420 |
| 6,596,019 | B2 | 7/2003 | Turner et al. | 607/108 |
| 6,647,552 | B1 | 11/2003 | Hogan | 2/114 |
| 6,694,522 | B1 | 2/2004 | Neal | 2/114 |
| 6,792,622 | B2 | 9/2004 | Graves | 2/114 |
| 6,799,332 | B2 | 10/2004 | Hatton | 2/114 |
| 6,800,087 | B2 * | 10/2004 | Papay et al. | 607/104 |
| 6,851,125 | B2 | 2/2005 | Fujikawa et al. | 2/51 |
| 6,876,884 | B2 | 4/2005 | Hansen et al. | 607/98 |
| 6,994,720 | B2 * | 2/2006 | Gammons | 607/104 |
| 7,001,416 | B2 | 2/2006 | Augustine et al. | 607/104 |
| 7,226,454 | B2 | 6/2007 | Albrecht et al. | 607/104 |
| 7,276,076 | B2 | 10/2007 | Bieberich | 607/108 |
| 7,291,163 | B2 * | 11/2007 | Gammons | 607/104 |
| 7,364,584 | B2 | 4/2008 | Anderson | 607/108 |
| 2005/0015127 | A1 | 1/2005 | Bieberich | 607/104 |
| 2005/0143796 | A1 | 6/2005 | Augustine et al. | 607/104 |
| 2006/0047332 | A1 | 3/2006 | Malmberg et al. | 607/104 |
| 2006/0122671 | A1 | 6/2006 | Albrecht et al. | 607/104 |
| 2006/0122672 | A1 | 6/2006 | Anderson | 607/104 |
| 2006/0147320 | A1 | 7/2006 | Hansen et al. | 417/313 |
| 2006/0184216 | A1 | 8/2006 | Van Duren | 607/104 |
| 2006/0184217 | A1 | 8/2006 | Van Duren | 607/104 |
| 2006/0184218 | A1 | 8/2006 | Bieberich | 607/104 |
| 2006/0259104 | A1 | 11/2006 | Panser et al. | 607/104 |
| 2007/0093882 | A1 | 4/2007 | Anderson et al. | 607/104 |
| 2007/0093883 | A1 | 4/2007 | Anderson et al. | 607/104 |
| 2007/0093884 | A1 | 4/2007 | Anderson et al. | 607/104 |
| 2007/0093885 | A1 | 4/2007 | Anderson et al. | 607/104 |
| 2007/0239239 | A1 | 10/2007 | Albrecht et al. | 607/96 |
| 2008/0027521 | A1 | 1/2008 | Bieberich | 607/96 |
| 2008/0027522 | A1 | 1/2008 | Bieberich | 607/96 |
| 2008/0125840 | A1 | 5/2008 | Anderson | 607/104 |

FOREIGN PATENT DOCUMENTS

| | | |
|---|---|---|
| GB | 1 462 033 | 1/1997 |
| SE | 525 415 | 2/2005 |
| WO | WO 97/14381 A1 | 4/1997 |
| WO | WO 98/48652 | 11/1998 |
| WO | WO 00/62726 | 10/2000 |
| WO | WO03/086500 A3 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2007/047917 A1 | 4/2007 |
| WO | WO 2008/013603 | 1/2008 |
| WO | WO 2008/091486 | 7/2008 |

OTHER PUBLICATIONS

International Search Report and Written Opinion in PCT/US2006/004644, mailed Dec. 18, 2006.

EPO Examination Report mailed Oct. 24, 2006, in EPO3719690.4-1526, EP Regional Phase of PCT/US2003/11128 (published as WO/2003/086500).

P.O. Fanger, Thermal Comfort: Analysis and Applications in Environmental Engineering, Danish Technical Press, 1970, pp. 5-67.

C.B. Mahony & J. Odom, Maintaining intraoperative normothermia: A meta-analysis of outcomes with costs. *AANA Journal.* Apr. 1999. v. 67, No. 2:155-164.

EPO Examination Report mailed Dec. 17, 2007, in EPO3719690.4-1526, EP Regional Phase of PCT/US2003/11128 (published as WO/2003/086500).

International Search Report and Written Opinion in PCT/US2005/025355, mailed Dec. 1, 2005.

International Search Report and Written Opinion in PCT/US2005/043968, mailed Apr. 19, 2006.

International Search Report and Written Opinion in PCT/US2005/044214, mailed Apr. 19, 2006.

International Search Report and Written Opinion in PCT/US2007/013073, mailed Nov. 9, 2007.

* cited by examiner

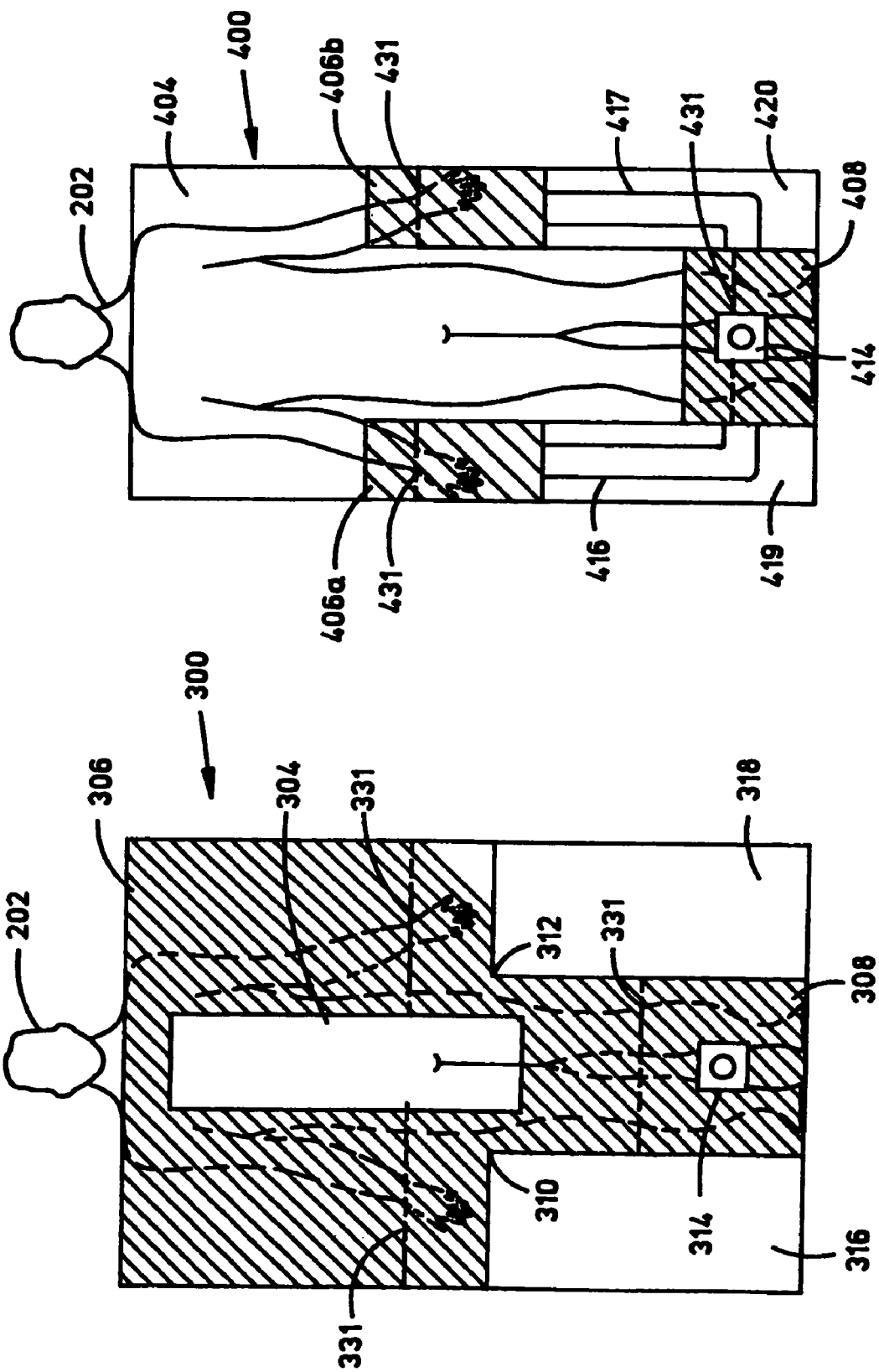

THERMAL BLANKET FOR WARMING THE LIMBS

RELATED APPLICATIONS

This application contains subject matter related to the subject matter of the following patent applications, all commonly owned herewith:

Patent Cooperation Treaty (PCT) Application No. PCT/US2003/011128, filed Apr. 10, 2003, entitled "Patient Comfort Apparatus and System", and published on Oct. 23, 2003 under Publication No. WO 2003/086500;

Patent Cooperation Treaty (PCT) Application No. PCT/US2005/025355, filed Jul. 18, 2005, entitled "Perioperative Warming Device", and published on Feb. 23, 2006 under Publication No. WO 2006/020170;

Patent Cooperation Treaty (PCT) Application No. PCT/US2005/043968, filed Dec. 6, 2005, entitled "Warming Device with Varied Permeability", and published on Jun. 15, 2006 under Publication No. WO 2006/062910;

Patent Cooperation Treaty (PCT) Application No. PCT/US2005/044214, filed Dec. 6, 2005, entitled "Warming Device", and published on Jun. 15, 2006 under Publication No. WO 2006/063027;

Patent Cooperation Treaty (PCT) Application No. PCT/US2006/004644, filed Feb. 9, 2006, entitled "Warming Device for Perioperative Use", and published on Aug. 17, 2006 under Publication No. WO2006/086587;

Patent Cooperation Treaty (PCT) Application No. PCT/US2006/041028, filed Oct. 19, 2006, entitled "Multifunction Warming Device for Perioperative Use", and published on Apr. 26, 2007 under Publication No. WO 2007/047917;

Patent Cooperation Treaty (PCT) Application No. PCT/US2007/013073, filed Jun. 1, 2007, entitled "Warming Device", published on Jan. 31, 2008 under Publication No. WO2008/013603;

Patent Cooperation Treaty (PCT) Application No. PCT/US2008/000141, filed Jan. 4, 2008, entitled "Convective Warming Device With a Drape", published on Jul. 31, 2008 under Publication No. WO 2008/091486;

U.S. patent application Ser. No. 10/411,865, filed Apr. 10, 2003, entitled "Patient Comfort Apparatus and System" and published on Oct. 16, 2003 under Publication No. U.S. 2003/0195596, now U.S. Pat. No. 7,001,416;

U.S. patent application Ser. No. 10/508,319,371(c) date Mar. 3, 2005, entitled "Patient Comfort Apparatus and System" and published on Jun. 30, 2005 under Publication No. US 2005/0143796;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/005,883, filed Dec. 7, 2004, entitled "Warming Device with Varied Permeability" and published on Jun. 8, 2006 under Publication No. US 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. US 2006/0122672;

U.S. patent application Ser. No. 11/057,396, filed Feb. 11, 2005, entitled "Perioperative Warming Device", now U.S. Pat. No. 7,276,076;

U.S. patent application Ser. No. 11/057,403, filed Feb. 11, 2005, entitled "Warming Device for Perioperative Use," published on Aug. 17, 2006 under Publication No. US 2006/0184217";

U.S. patent application Ser. No. 11/057,404, filed Feb. 11, 2005, entitled "Clinical Garment for Comfort Warming and Prewarming," published on Aug. 17, 2006 under Publication No. US 2006/0184218";

U.S. patent application Ser. No. 11/260,706, filed Oct. 27, 2005, entitled "Patient Comfort Apparatus and System", and published on Mar. 9, 2006 under Publication No. US 2006/0052853;

U.S. patent application Ser. No. 11/363,136, filed Feb. 27, 2006, entitled "Forced Air Warming Unit" and published on Jul. 6, 2006 under Publication No. US 2006/0147320;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,432, filed Oct. 19, 2006, entitled "Multifunction Warming Device for Perioperative Use", and published on Apr. 26, 2007 under Publication No. US 2007/0093882;

U.S. patent application Ser. No. 11/583,477, filed Oct. 19, 2006, entitled "Multifunction Warming Device with Provision for Being Secured", and published on Apr. 26, 2007 under Publication No. US 2007/0093883;

U.S. patent application Ser. No. 11/583,480, filed Oct. 19, 2006, entitled "Multifunction Warming Device with Provision for Warming Hands", and published on Apr. 26, 2007 under Publication No. US 2007/0093884;

U.S. patent application Ser. No. 11/583,481, filed Oct. 19, 2006, entitled "Multifunction Warming Device with an Upper Body Convective Apparatus", and published on Apr. 26, 2007 under Publication No. US 2007/0093885;

U.S. patent application Ser. No. 11/656,777, filed Jan. 23, 2007, entitled "Convective Warming Device With a Drape";

U.S. patent application Ser. No. 11/704,547, filed Feb. 9, 2007, entitled "A Forced Air Warming Unit";

U.S. patent application Ser. No. 11/801,292, filed May 9, 2007, entitled "Warming Device with Varied Permeability", and published on Oct. 11, 2007 under Publication No. US 2007/023939;

U.S. patent application Ser. No. 11/899,872, filed Sep. 7, 2007, entitled "Perioperative Warming Method", and published on Jan. 31, 2008 under Publication No. US 2008/0027522; and, U.S. patent application Ser. No. 11/899,928, filed Sep. 7, 2007, entitled "Perioperative Warming Device" and published on Jan. 31, 2008 under Publication No. US 2008/0027521.

BACKGROUND OF THE INVENTION

A convective thermal blanket for preoperative therapeutic and comfort warming includes an inactive surface region adapted to lie against the anterior thoracic and/or abdominal area of a person extending at least from the thighs to the abdomen of the person and active surface regions adapted to circulate warmed air to limbs of the person.

Use of the term "convective" to denote the transfer of heat by the circulation of warmed air from a convective thermal blanket to a body refers to the principal mode of heat transfer, it being understood that heat may at the same time be transferred between a thermal blanket and a body by conduction and radiation, although not to the degree of convection.

Convective thermal blankets that transfer heat to a human body are known. For example, there are blankets that receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. These blankets are typically called "convective thermal blankets" or "covers"; for convenience, in this application they shall be called, simply, "thermal blankets." Arizant Healthcare Inc., the assignee of this application, makes and sells such blankets under the BAIR HUGGER® brand. One such blanket is the Model 522 Upper Body Blanket.

The term "perioperative" is defined in the PDR Medical Dictionary, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. *AANA Journal.* 4/99; 67, 2:155-164.), therapeutic warming is employed during at least the intraoperative period in order to prevent or mitigate a constellation of effects that result from hypothermia. In fact, it is increasingly manifest that maintenance of normothermia perioperatively enhances the prospects for a quick, successful recovery from surgery. The effectiveness of therapeutic warming depends upon delivery of enough heat to a patient's body to raise the patient's core body temperature to, or maintain it within, a narrow range, typically near 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort." Of course, therapeutic warming may also comfort a patient by alleviating shivering or a feeling of being cold, but this is a secondary or ancillary effect. Thermal comfort is a subjective notion; however, the environmental conditions necessary to produce a sense of thermal comfort in a population of human beings are known and well tabulated. For example, Fanger (*Thermal Comfort: Analysis and Applications of Environmental Engineering.* Danish Technical press, Copenhagen, 1970) defines thermal comfort as "that condition of mind which expresses satisfaction with the thermal environment." Even when a patient is normothermic, less than ideal conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Therapeutic warming may be provided by a convective thermal blanket that receives and distributes warmed, pressurized air in an inflatable pneumatic structure and then expels the distributed air through one or more surfaces toward a patient in order to prevent or treat hypothermia in the patient. An example of such use is found in U.S. Pat. No. 6,524,332, "System and Method for Warming a Person to Prevent or Treat Hypothermia", commonly owned with this application. Comfort warming by convective means is described in the referenced U.S. Patent Application, and the referenced Publication No. WO 03/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced air warming unit, a heater unit, etc.), a convective device, and a flexible conduit or air hose connecting the heater/blower unit with the convective device. Use of such a system for a particular type of warming requires delivery of warmed air through the convective device at parametric values that achieve a particular objective. The conditions by which a convective device such as a presently-designed thermal blanket produces thermal comfort in normothermic individuals at steady state are significantly different from those necessary to treat hypothermia. Typically the conditions for thermal comfort are met in a comfort warming system with a relatively low capacity heater/blower unit, while those in a therapeutic warming system are achieved with a relatively high capacity heater/blower unit. The different capacities have led to use of air hoses with different capacities, with those delivering air flow for thermal comfort typically having smaller diameters than those serving a therapeutic warming requirement. The result is a divergence of designs leading to installation of different air delivery infrastructures for therapeutic and comfort warming.

In some perioperative circumstances, the indiscriminate use of thermal blankets for comfort warming during the intraoperative and postoperative periods may expose the patient to several dangers. In particular, the use of a thermal blanket to produce comfort warming when therapeutic warming is indicated may significantly prolong the time necessary to produce normothermia. Thus it is sometimes advantageous and even safe to restrict the use of comfort warming to those settings where it is appropriate, which are principally in the preoperative period.

The application of warmed air to the limbs by a comfort warming system produces the sense of well-being that characterizes comfort warming because of the high density of thermoreceptors in the arms and legs. Warming the peripheral body regions produces a greater comfort response than thermal stimulation of the anterior or posterior abdominal and thoracic body regions. One surprising result of warming preoperatively by heating the limbs is that the increase of thermal energy content in the body's periphery prevents or reduces the core temperature drop caused by core-to-periphery redistribution. Thus, while warming the limbs preoperatively does not produce an increase in core body temperature, it does prevent that temperature from dropping once anesthesia is initiated. Warming the limbs preoperatively in order to prevent or delay a drop in core body temperature may be referred to as "prewarming."

However, most presently-designed thermal blankets are designed to warm the anterior thoracic and/or abdominal regions of the body. They are not particularly well adapted to provide prewarming or comfort warming because of the low density of thermo-receptors in the central anterior region of the body. The comfort warming devices taught in PCT Publication No. WO 03/086500 are very effective for ambulatory patients put in control of the comfort warming parameters. However, these devices are not particularly well-suited to supine patients who are being prepared for surgery. In particular, they do not provide prewarming and/or comfort warming that is focused on the limbs.

SUMMARY OF THE INVENTION

In one aspect, a thermal blanket includes a surface, an inactive region of the surface adapted to lie against the anterior or posterior surface of a person extending at least from the thighs to the abdomen of the person, active regions of the surface adapted to circulate air to limbs of the person, and an inflatable pneumatic structure adapted to distribute air to the active regions.

In another aspect, the active regions are separate active regions of the surface which surround the inactive region, and the pneumatic structure includes at least one manifold connecting the separate active regions.

In yet another aspect, the active regions include a first active region adapted to circulate air to the shoulders and non-outstretched arms of the person, and a second active region in communication with the first active region and adapted to circulate air to the adjacently-disposed lower legs of the person.

BRIEF DESCRIPTION OF THE DRAWINGS

FIG. 3 is a top plan view of another thermal blanket for warming the limbs of a person.

FIG. 4 is a top plan view of yet another thermal blanket for warming the limbs of a person.

SPECIFICATION

A thermal blanket receives and distributes at least one stream of warmed pressurized air in a pneumatic structure for being disposed on, adjacent, or next to the core and/or the limbs of a person's body. The thermal blanket is inflatable. When pressurized with warmed air, the thermal blanket emits warmed air through one or more of its surfaces toward a person's body.

Figure 1:
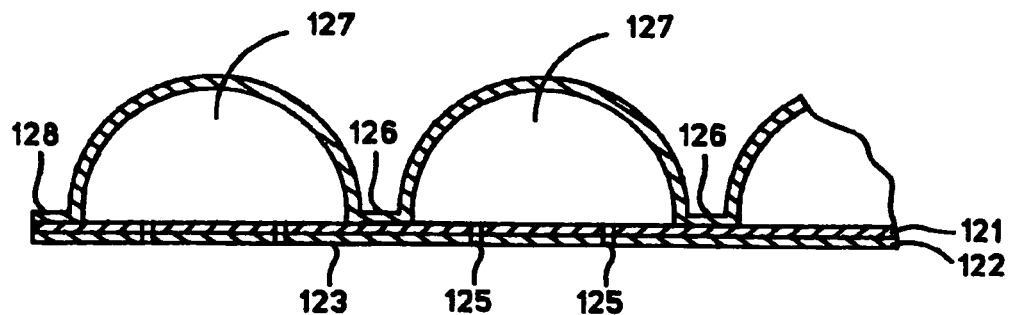
FIG. 1 is a side sectional drawing showing construction details of a thermal blanket for comfort warming.

Thermal blanket construction is well known. Examples of specific constructions are given in U.S. Pat. Nos. 5,620,482, 5,443,488, 5,360,439, and 5,304,213. For example, as shown in FIG. 1 a thermal blanket (shown inflated) is constructed from first and second sheets 121 and 122 of flexible material that are brought together and sealed at their peripheries (one indicated at 128) and at a plurality of stake points 126 within the peripheries. The sheets 121, 122 may be single layer or laminated structures capable of being joined by sealing using heat, glue, ultrasonic welds or any equivalent technique. The sheet materials may be made of any one or a combination of extruded synthetics and/or woven or non-woven fabrics of synthetic, natural, or wood pulp material. The first sheet 121, which is typically impermeable, faces away from a person when the thermal blanket is deployed. The second sheet 122 is permeable, either from having apertures formed in it during construction of the thermal blanket or from the construction of the sheet itself from material with interstices. Because of its construction, the second sheet 122 has a surface 123 adapted to face a person when the thermal blanket is deployed for use. One or more inlet ports (not shown) are constructed in the first sheet 121, through the seal between the first and second sheets, or through the edge of the thermal blanket. Each inlet port is capable of receiving and retaining the nozzle of an air hose. The inlet ports and/or the nozzles may be adapted to accommodate heater/blower units of different types. The space 127 between the sealed sheets constitutes a pneumatic structure that inflates in response to pressurized flowing into an inlet port through an air hose and distributes the pressurized air over the second sheet 122. When the thermal blanket is used, the pressurized air circulates through the surface 123 to the patient. If warmed, the air circulated through the surface 123 warms the patient. These structures are manufactured by continuous web manufacturing lines that may incorporate spiked rollers to form apertures and heated platens with inscribed patterns to join the sheets by patterned heat seals. The resulting thermal blankets are flexible, foldable, inflatable devices.

In the following description, thermal blankets with structures based upon the construction illustrated in FIG. 1, or any other equivalent construction, will be described. Each of these thermal blankets has at least one surface adapted to face a patient when the thermal blanket is deployed for use. This surface has "inactive" and "active" regions. In this regard, an inactive region is a region of the surface through which air does not circulate when the thermal blanket is inflated. The inactive region may or may not be permeable. If impermeable, air cannot circulate through the inactive region because of its construction. If permeable, air cannot circulate through the inactive region because it is not in communication with the inflatable pneumatic structure of the blanket. An active region is a region through which air does circulate when the thermal blanket is inflated. An active region is both permeable and in communication with the inflatable pneumatic structure of the blanket.

A thermal blanket for warming the limbs to provide prewarming and/or comfort warming includes a surface adapted to face a person's body. The surface includes at least one inactive region which is adapted to lie against a body portion including the anterior or posterior skin surface of a person extending at least from the thighs to the abdomen of the person. The surface also includes active regions adapted to circulate air to limbs of the person. An inflatable pneumatic structure of the thermal blanket is adapted to distribute pressurized air to the active regions.

Figure 2A:
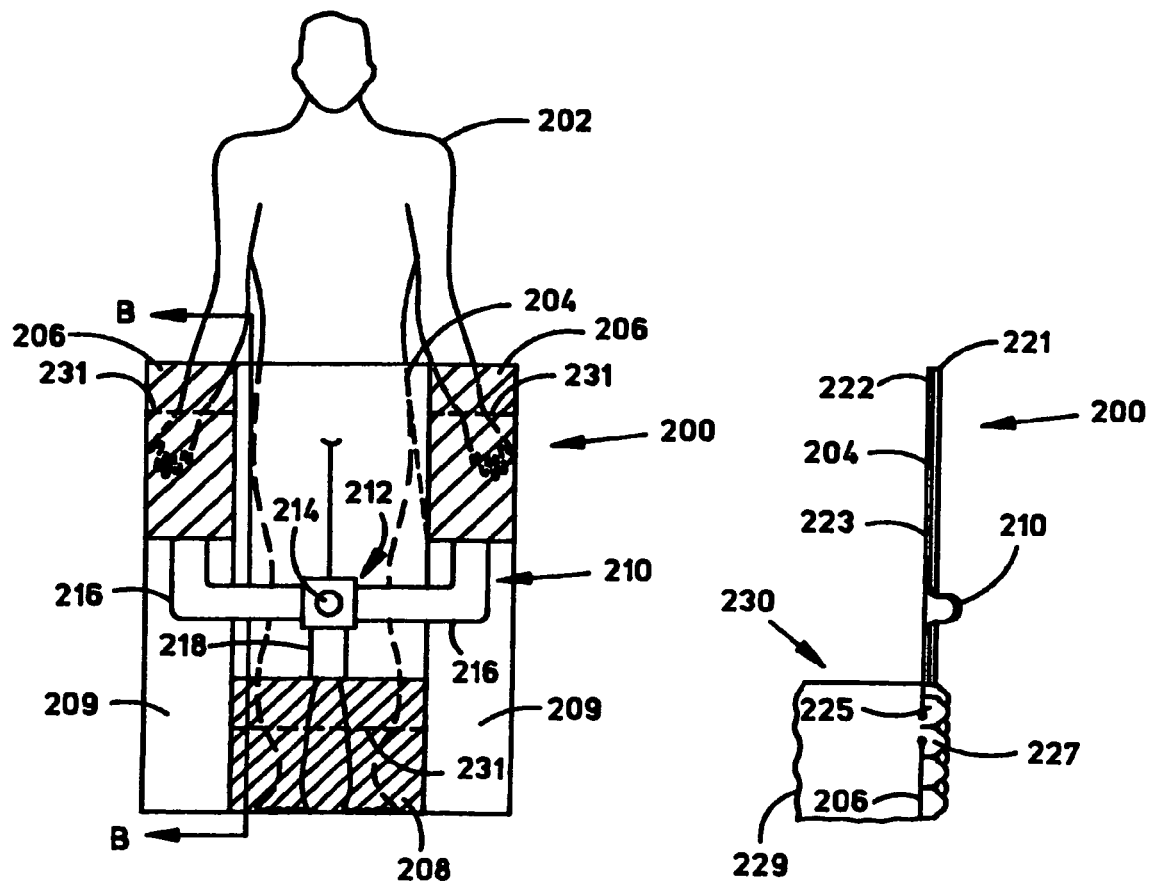
FIG. 2A is a top plan view of a thermal blanket for warming the limbs of a person.

FIG. 2A is a plan view of a thermal blanket 200 for warming the limbs to provide prewarming or comfort warming. This thermal blanket 200 extends from the mid-abdominal region to the feet of a person 202. Although the view of the thermal blanket seen in the drawing shows the surface that faces away from the person, various aspects of the surface which is adapted to face the person are indicated by shading. In this regard, the shaded areas indicate the active regions of the surface which is adapted to face the person, while the clear areas indicate the inactive regions of the surface which is adapted to face the person. The surface which is adapted to face the person includes a quadrilateral region 204 that is inactive. The inactive region 204 is adapted to lie against a portion of the anterior body surface of the person 202 extending at least from the thighs to the abdomen. The surface includes two active regions 206 that flank the upper portion of the inactive region 204, extending from the inactive region 204 to respective sides of the thermal blanket 200. Each of the two active regions 206 is adapted to lie against a portion of a respective arm of the person, extending from the forearm to the fingers. The surface also includes a third active region 208 adapted to lie against the adjacently-disposed legs of the person, from the mid-calves to the toes. Two elongate peripheral inactive regions 209 of the surface flank the third active region and join the inactive region 204 in the middle section of the thermal blanket 200. A manifold 210 is formed in the thermal blanket 200, preferably in the inactive sections 204, 209. The manifold has a central node 212 where an inlet port 214 is located, extensions 216 that connect the node 212 to the active regions 206 and an extension 218 connecting the node 212 to the active region 208.

Figure 2B:
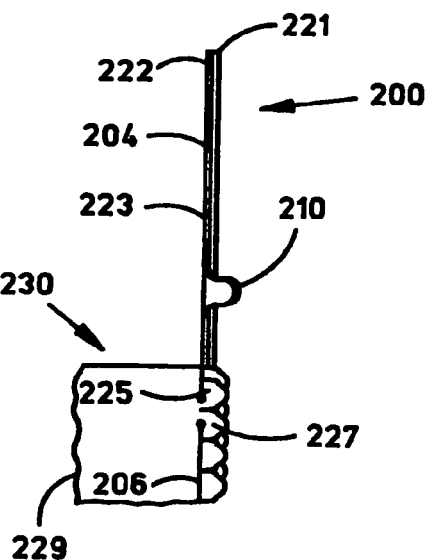
FIG. 2B is a cross section of the thermal blanket of FIG. 2B taken along line B-B in FIG. 2A.

The thermal blanket 200 of FIG. 2A may be made using the construction techniques described above, or any other equivalent construction. One illustrative example is shown in FIG. 2B. In order to more clearly illustrate the structural features being described, airflow through the thermal blanket 200 is presumed, accompanied by inflation. Of course, without airflow the thermal blanket would have a different contour. In FIG. 2B, the thermal blanket 200 is made by sealing two sheets 221 and 222 together. The surface 223 of the sheet 222 faces a patient. At least the sheet 222 has apertures (or interstices) 225. Pressurized air circulates through the apertures in the sheet 221 in an active region; no pressurized air circulates through apertures in either sheet 221 or 222 in an inactive region. In the case where apertures are formed in the sheet during manufacture of the thermal blanket 200, either no apertures would be formed in the inactive regions, or the inactive regions would be sealed to prevent circulation of air to those regions. In the case the sheet 222 is a permeable material, it may be treated during the process of manufacturing the thermal blanket 200 to reduce, disable or eliminate permeability in the inactive regions 204 and 209. The circulation of pressurized air to the inactive regions of the surface 223 may be blocked in any manner suitable to construction of the thermal blanket 200. In this regard, the sheets 221 and 222 may be continuously sealed together at the borders between the active and inactive regions to prevent circulation from the active to the inactive regions, or sealed together over the entirety of the inactive regions. In the first case, the seal between active and inactive regions would be interrupted only where a section of the manifold 210 transits the border between the regions. The manifold 210 is a continuous tubular structure that provides communication between the active regions 206 and 208. The tubes of the manifold 210 may be formed by continuous seals between the two sheets along the periphery of the manifold 210. Alternatively, in the case where the sheets 221 and 222 are sealed together within the inactive regions, the sheets would not be sealed in the footprint of the manifold 210. Constructed as the described, a pneumatic structure including the manifold 210 and space 227 between the sheets 221 and 222 in the active regions 206 and 208 circulates pressurized air from the inlet port 214 through the manifold 210 to the active regions 206, where the air is circulated through apertures 225 to the limbs of a patient for prewarming and/or comfort warming. The structure of the thermal blanket 200 may further include retainers such as pockets, tie straps, or other equivalent elements to retain the thermal blanket on portions of the limbs to be warmed by the active regions of the thermal blanket 200. In FIG. 2B for example, a pocket 229 with at least one open end 230 is shown receiving the feet of the person 202 near the active region 208. The pocket 229 may be formed by attaching a sheet of material to the surface 223 along at least the traces of the seals between the active region 208 and the flanking inactive regions 209. Representative locations for these retainers are indicated by the dashed lines 231 in FIG. 2A which represent open ends of such retainers.

In FIG. 3, a thermal blanket 300 for comfort warming is shown in a plan view. This thermal blanket 300 extends from the neck region to the feet of the person 202. Although the view of the thermal blanket seen in the drawing shows the surface that faces away from the person, various aspects of the surface which is adapted to face the person are indicated by shading. In this regard, the shaded areas indicate the active regions of the surface which is adapted to face the person, while the clear areas indicate the inactive regions of the surface which is adapted to face the person. The surface which is adapted to face the person includes a region 304 that is inactive. The inactive region 304 is adapted to lie against a body portion including the anterior surface of the person 202 extending at least from the thighs to the chest. A first active region 306 of the surface is adapted to circulate pressurized air to the shoulders and non-outstretched arms of the person 202. A second active region 308 of the surface is adapted to circulate pressurized air to the adjacently-disposed lower legs of the person. The first and second active regions 306 and 308 are in communication with each other at 310 and 312, where pressurized air can circulate between the active regions to the limbs of a patient for prewarming and/or comfort warming. An inlet port 314 is provided into a pneumatic structure which distributes pressurized air to the active regions 306 and 308. Although only a single inlet port is shown in FIG. 3, another port may be provided in either of the active regions 306 and 308. The surface includes quadrilateral inactive regions 316 and 318 that flank the active region 308 beneath the active region 306. The thermal blanket may be constructed from two sheets of material using materials and techniques descried above in connection with FIGS. 2A and 2B, which would result in pneumatic structure including space between the sheets in the active regions of the thermal blanket 300. Retainers such as pockets tie straps, or other equivalent elements may be provided on the surface as described above in connection with FIGS. 2A and 2B to retain the thermal blanket on portions of the limbs to be warmed by the active regions of the thermal blanket 300. Representative locations for such retainers are indicated by the dashed lines 331 in FIG. 3 which represent open ends of such retainers.

In FIG. 4, a thermal blanket 400 for comfort warming is shown in a plan view. This thermal blanket 400 extends from the neck region to the feet of the person 202. Although the view of the thermal blanket seen in the drawing shows the surface that faces away from the person, various aspects of the surface which is adapted to face the person are indicated by shading. In this regard, the shaded areas indicate the active regions of the surface which is adapted to face the person, while the clear areas indicate the inactive regions of the surface which is adapted to face the person. The surface which is adapted to face the person includes a first region 404 that is inactive. The inactive region 404 is adapted to lie against a body portion including substantially the entire anterior surface of the body of the person 202 extending at least from the calves to the chest, shoulders and upper arms, without circulating air to the body portion. First and second active regions 406a and 406b of the surface are adapted to circulate air to the lower portions of the arms and the hands of the person 202 for prewarming and/or comfort warming. A third active region 408 of the surface is adapted to circulate pressurized air to the adjacently-disposed lower legs of the person, from the calves to the feet, to the limbs of a patient for prewarming and/or comfort warming. A first manifold 416 connects the first and third active regions 406a and 408. A second manifold 417 connects the second and third active regions 406b and 408. An inlet port 414 is provided into a pneumatic structure which distributes pressurized air to the active regions 406a, 406b, and 408. Although only a single inlet port is shown in FIG. 4, another port may be provided in either or both of the active regions 406*a* and 406*b*. The surface includes quadrilateral inactive regions 419 and 420 that flank the active region 408 beneath the active regions 406*a* and 406*b*. The thermal blanket 400 may be constructed from two sheets of material using materials and techniques descried above in connection with FIGS. 2A and 2B, which would result in a pneumatic structure including space between the sheets in the active regions of the thermal blanket 400 and the manifolds 416 and 417. Retainers such as pockets, tie straps, or other equivalent elements may be provided on the surface as described above in connection with FIGS. 2A and 2B to retain the thermal blanket on portions of the limbs to be warmed by the active regions of the thermal blanket 400. Representative locations for such retainers are indicated by the dashed lines 431 in FIG. 4 which represent open ends of such retainers.

Manifestly, those skilled in the art will appreciate that many variations of the thermal blankets illustrated and discussed herein may be implemented without departing from the inventive principle of this thermal blanket for comfort warming. For example, the active regions of the thermal blanket 200 may be served by two manifolds in the manner illustrated for the thermal blanket 400. Similarly, the thermal blanket 400 may be served by a single manifold in the manner illustrated for the thermal blanket 200. Also, the particular design of a thermal blanket may reposition the inlet ports shown or may provide additional inlet ports in other locations.

The invention claimed is:

1. A thermal blanket for warming limbs of a person during a preoperative period, comprising:
    a surface for facing the person;
    a plurality of inactive regions of the surface of which one inactive region is adapted to lie against a body portion of the person which extends at least from the thighs to the abdomen of the person;
    a plurality of separate active regions of the surface adapted to circulate pressurized air to limbs of the person; and
    an inflatable pneumatic structure to distribute warmed pressurized air to the active regions;
    the pneumatic structure including at least one manifold connecting the active regions.

2. The thermal blanket of claim 1, further including at least one retainer on the surface to receive a portion of one of the limbs.

3. The thermal blanket of claim 1, wherein the pneumatic structure includes at least two manifolds to conduct pressurized air to the active regions.

4. The thermal blanket of claim 3, further including at least one retainer on the surface to receive a portion of one of the limbs.

5. The thermal blanket of claim 1, wherein the active regions include three active regions.

6. The thermal blanket of claim 1, wherein the active regions surround the one inactive region.

7. The thermal blanket of claim 1, wherein the one inactive region has a rectangular shape.

8. The thermal blanket of claim 7, wherein the active regions include;
    a first active region adapted to circulate pressurized air to the shoulders and non-outstretched arms of the person; and
    a second active region in communication with the first active region, the second active region adapted to circulate pressurized air to adjacently-disposed lower leg portions of the person.

9. A thermal blanket for warming the limbs of a person, comprising:
    a surface for facing the person;
    an inactive region of the surface, the inactive region adapted to lie against a body portion of the person extending at least from the calves to the abdomen of the person;
    at least three separate active regions of the surface adapted to circulate pressurized air to limbs of the person; and
    an inflatable pneumatic structure to distribute warmed pressurized air to the active regions; and
    the pneumatic structure including at least one manifold connected to the active regions.

10. The thermal blanket of claim 9, further including at least one retainer on the surface to receive a portion of one of the limbs.

11. The thermal blanket of claim 9, wherein the active regions are disposed around the inactive region.

12. The thermal blanket of claim 11, wherein the inactive region has a rectangular shape.

13. The thermal blanket of claim 12, wherein the three active regions include first and second active regions adapted to circulate pressurized air to the arms of the person and a third active region adapted to circulate pressurized air to the legs of the person.

14. The thermal blanket of claim 13, wherein the at least one manifold includes a first manifold connected to the first and third active regions and a second manifold connected to the second and third active regions.

15. A thermal blanket for warming the limbs of a person, comprising:
    a surface for facing the person;
    an inactive region of the surface, the inactive region adapted to lie against a body portion of the person extending at least from the calves to the shoulders of the person;
    at least three separate active regions of the surface adapted to circulate warmed pressurized air to limbs of the person;
    an inflatable pneumatic structure to distribute warmed pressurized air to the active regions; and
    the pneumatic structure including at least one manifold connecting the active regions.

16. The thermal blanket of claim 15, further including at least one retainer on the surface to receive a portion of one of the limbs.

17. The thermal blanket of claim 15, wherein the active regions are disposed around the inactive region.

18. The thermal blanket of claim 17, wherein the active regions include:
    a first active region adapted to circulate pressurized air to a portion of one arm of the person;
    a second active region adapted to circulate pressurized air to a portion of the other arm of the person; and
    a third active region adapted to circulate pressurized air to portions of the adjacently-disposed legs of the person.

19. The thermal blanket of claim 18 wherein the at least one manifold includes:
    a first manifold connected to the first and third active regions; and
    a second manifold connected to the second and third active regions.

20. The thermal blanket of claim 18 wherein the at least one manifold includes a manifold connected to all three active regions.

* * * * *

UNITED STATES PATENT AND TRADEMARK OFFICE
CERTIFICATE OF CORRECTION

| | | |
|---|---|---|
| PATENT NO. | : 7,520,889 B2 | Page 1 of 1 |
| APPLICATION NO. | : 11/057397 | |
| DATED | : April 21, 2009 | |
| INVENTOR(S) | : Albert P. Van Duren | |

It is certified that error appears in the above-identified patent and that said Letters Patent is hereby corrected as shown below:

Title Page, Page 2
Under the heading U.S. PATENT DOCUMENTS
  column 1, line 6, replace "5,443,488 A 8/1995 Namenye et al. 607/107" with "5,443,488 A 8/1995 Namenye et al. 607/104".

Under the heading OTHER PUBLICATIONS
  column 2, add "Porta-Chill-The Portable Air-Chiller-Brochure, http://www.portachil.com/, 12/03/2002".

Column 6, line 14
Add the word "air" after the word "pressurized".

Column 8, line 32
Delete the word "descried" and replace it with the word "described".

Column 9, line 7
Delete the word "descried" and replace it with the word "described".

Signed and Sealed this

Twenty-sixth Day of January, 2010

David J. Kappos
*Director of the United States Patent and Trademark Office*